(12) United States Patent
Pingleton et al.

(10) Patent No.: US 8,529,719 B2
(45) Date of Patent: Sep. 10, 2013

(54) METHOD OF MAKING MEDICAL TUBING HAVING VARIABLE CHARACTERISTICS USING THERMAL WINDING

(75) Inventors: Edward D Pingleton, San Juan Capistrano, CA (US); Matthew N Petrime, Los Angeles, CA (US); Ghassan Sakakine, Rancho Santa Margarita, CA (US); Jeremy J Albrecht, Ladera Ranch, CA (US); Nabil Hilal, Laguna Niguel, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 1439 days.

(21) Appl. No.: 11/750,847

(22) Filed: May 18, 2007

(65) Prior Publication Data

US 2007/0215268 A1 Sep. 20, 2007

Related U.S. Application Data

(60) Continuation-in-part of application No. 10/766,138, filed on Jan. 28, 2004, now abandoned, and a continuation-in-part of application No. 11/319,870, filed on Dec. 28, 2005, now Pat. No. 7,534,317, which is a division of application No. 10/298,116, filed on Nov. 15, 2002, now Pat. No. 7,005,026.

(60) Provisional application No. 60/747,644, filed on May 18, 2006.

(51) Int. Cl.
*B32B 37/00* (2006.01)

(52) U.S. Cl.
USPC ... 156/173; 156/169; 156/244.11; 156/308.2; 156/309.6; 156/309.9

(58) Field of Classification Search
USPC ............... 156/169, 173, 175, 244.11, 308.2, 156/309.6, 309.9
See application file for complete search history.

(56) References Cited

U.S. PATENT DOCUMENTS

| 2,130,586 A | 9/1938 | Huston |
| 2,467,999 A * | 4/1949 | Stephens ................ 138/144 |
| 2,688,343 A | 9/1954 | Cuddeback |

(Continued)

FOREIGN PATENT DOCUMENTS

| EP | 0265915 A2 * | 5/1988 |
| EP | 0 421 650 A | 4/1991 |

(Continued)

OTHER PUBLICATIONS

International Searching Authority International Search Report and the Written Opinion of the International Searching Authority for International application No. PCT/US07/69282 mailed Jan. 16 2008.

(Continued)

*Primary Examiner* — Jeff Aftergut
(74) *Attorney, Agent, or Firm* — Rimas T. Lukas; Patrick Y. Ikehara; Cynthia A. Bonner

(57) ABSTRACT

An efficient and cost-effective method of manufacturing a kink-resistant tube, wherein a coated wire is wound around a mandrel while simultaneously being heated to melt the coating, is provided.

22 Claims, 11 Drawing Sheets

(56) References Cited

U.S. PATENT DOCUMENTS

| | | | |
|---|---|---|---|
| 2,701,562 | A | 2/1955 | Michael et al. |
| 2,722,263 | A | 11/1955 | Beare et al. |
| 3,113,897 | A | 12/1963 | Gisle Skansen et al. |
| 3,226,767 | A | 1/1966 | Howell |
| 3,354,695 | A | 11/1967 | Szente |
| 3,477,891 | A | 11/1969 | Hawerkamp |
| 3,585,707 | A | 6/1971 | Stevens |
| 3,617,415 | A | 11/1971 | Hawerkamp |
| 3,618,613 | A | 11/1971 | Schulte |
| 3,910,808 | A | 10/1975 | Steward |
| 3,919,026 | A | 11/1975 | Mizutani et al. |
| 3,988,190 | A | 10/1976 | McWilliams |
| 4,010,054 | A * | 3/1977 | Bradt .................. 156/173 |
| 4,051,844 | A | 10/1977 | Chiulli |
| 4,078,957 | A | 3/1978 | Bradt |
| 4,135,869 | A | 1/1979 | Loyer |
| 4,302,261 | A | 11/1981 | Simkins et al. |
| 4,343,672 | A | 8/1982 | Kanao |
| 4,350,547 | A | 9/1982 | Kanao |
| 4,466,854 | A | 8/1984 | Hawerkamp |
| 4,470,941 | A | 9/1984 | Kurtz |
| 4,540,360 | A | 9/1985 | Leo |
| 4,586,923 | A | 5/1986 | Gould et al. |
| 4,605,990 | A | 8/1986 | Wilder et al. |
| 4,619,643 | A | 10/1986 | Bai et al. |
| 4,690,175 | A | 9/1987 | Ouchi et al. |
| 4,707,906 | A | 11/1987 | Posey |
| 4,811,743 | A | 3/1989 | Stevens |
| 4,818,460 | A | 4/1989 | Nied |
| 4,820,274 | A | 4/1989 | Choksi et al. |
| 4,826,423 | A | 5/1989 | Kemp et al. |
| 4,911,148 | A | 3/1990 | Sosnowski |
| 5,084,033 | A | 1/1992 | O'Neill |
| 5,092,950 | A | 3/1992 | Spoo et al. |
| 5,179,935 | A | 1/1993 | Miyagi |
| 5,180,376 | A | 1/1993 | Fischell |
| 5,195,968 | A | 3/1993 | Lundquist et al. |
| 5,228,441 | A | 7/1993 | Lundquist |
| 5,254,088 | A | 10/1993 | Lundquist et al. |
| H1261 | H | 12/1993 | Gibson et al. |
| 5,273,535 | A | 12/1993 | Edwards et al. |
| 5,275,151 | A | 1/1994 | Shockey et al. |
| 5,284,128 | A | 2/1994 | Hart |
| 5,304,131 | A | 4/1994 | Paskar |
| 5,315,996 | A | 5/1994 | Lundquist |
| 5,322,064 | A | 6/1994 | Lundquist |
| 5,328,467 | A | 7/1994 | Edwards et al. |
| 5,329,923 | A | 7/1994 | Lundquist |
| 5,342,299 | A | 8/1994 | Snoke et al. |
| 5,383,852 | A | 1/1995 | Stevens-Wright |
| 5,395,327 | A | 3/1995 | Lundquist et al. |
| 5,409,469 | A | 4/1995 | Schaerf |
| 5,429,127 | A | 7/1995 | Kolobow |
| 5,441,483 | A | 8/1995 | Avitall |
| 5,456,664 | A | 10/1995 | Heinzelman et al. |
| 5,462,527 | A | 10/1995 | Stevens-Wright et al. |
| 5,472,435 | A | 12/1995 | Sutton |
| 5,484,407 | A | 1/1996 | Osypka |
| 5,507,751 | A | 4/1996 | Goode |
| 5,509,910 | A | 4/1996 | Lunn |
| 5,512,035 | A | 4/1996 | Konstorum et al. |
| 5,531,721 | A | 7/1996 | Pepin et al. |
| 5,538,513 | A * | 7/1996 | Okajima .................. 604/527 |
| 5,558,737 | A | 9/1996 | Brown et al. |
| 5,632,734 | A | 5/1997 | Galel |
| 5,637,168 | A | 6/1997 | Carlson |
| 5,702,433 | A | 12/1997 | Taylor et al. |
| 5,709,665 | A | 1/1998 | Vergano et al. |
| 5,774,950 | A | 7/1998 | Stout |
| 5,792,116 | A | 8/1998 | Berg et al. |
| 5,836,925 | A | 11/1998 | Soltesz et al. |
| 5,840,031 | A | 11/1998 | Crowley |
| 5,863,366 | A | 1/1999 | Snow |
| 5,879,499 | A * | 3/1999 | Corvi .................. 156/175 |
| 5,888,436 | A | 3/1999 | Keith et al. |
| 5,891,088 | A | 4/1999 | Thompson et al. |
| 5,902,287 | A | 5/1999 | Martin |
| 5,935,102 | A | 8/1999 | Bowden et al. |
| 5,945,048 | A | 8/1999 | Ensinger |
| 5,947,940 | A | 9/1999 | Beisel |
| 5,976,075 | A | 11/1999 | Beane et al. |
| 6,007,531 | A | 12/1999 | Snoke et al. |
| 6,033,378 | A | 3/2000 | Lundquist et al. |
| 6,045,547 | A | 4/2000 | Ren |
| 6,198,974 | B1 | 3/2001 | Webster, Jr. |
| 6,203,732 | B1 | 3/2001 | Clubb et al. |
| 6,246,914 | B1 | 6/2001 | de la Rama |
| 6,263,224 | B1 | 7/2001 | West |
| 6,306,235 | B1 | 10/2001 | Henderson |
| 6,337,142 | B2 | 1/2002 | Harder |
| 6,368,316 | B1 | 4/2002 | Jansen et al. |
| 6,451,005 | B1 | 9/2002 | Saitou et al. |
| 6,464,632 | B1 | 10/2002 | Taylor |
| 6,485,455 | B1 | 11/2002 | Thompson et al. |
| 6,500,167 | B1 | 12/2002 | Webster, Jr. |
| 6,533,770 | B1 | 3/2003 | Lepulu et al. |
| 6,533,984 | B2 | 3/2003 | Curti |
| 6,537,405 | B1 | 3/2003 | Henderson et al. |
| 6,540,734 | B1 | 4/2003 | Chiu et al. |
| 6,599,265 | B2 | 7/2003 | Bon |
| 6,602,278 | B1 | 8/2003 | Thompson et al. |
| 6,605,171 | B1 | 8/2003 | Debalme et al. |
| 6,648,875 | B2 | 11/2003 | Simpson et al. |
| 6,652,506 | B2 | 11/2003 | Bowe et al. |
| 6,663,588 | B2 | 12/2003 | DuBois et al. |
| 6,669,886 | B1 | 12/2003 | Willard |
| 6,752,190 | B1 * | 6/2004 | Boll et al. .................. 156/433 |
| 6,776,765 | B2 | 8/2004 | Soukup et al. |
| 6,783,491 | B2 | 8/2004 | Saadat et al. |
| 6,804,866 | B2 | 10/2004 | Lemke et al. |
| D504,175 | S | 4/2005 | Westbrook |
| 6,916,306 | B1 | 7/2005 | Jenkins et al. |
| 6,976,987 | B2 | 12/2005 | Flores |
| 6,979,312 | B2 | 12/2005 | Shimada |
| 7,005,026 | B2 | 2/2006 | Brustad et al. |
| 7,534,317 | B2 | 5/2009 | Brustad et al. |
| 7,850,811 | B2 | 12/2010 | Hart et al. |
| 2001/0010247 | A1 | 8/2001 | Snow |
| 2001/0037084 | A1 | 11/2001 | Nardeo |
| 2002/0022762 | A1 | 2/2002 | Beane et al. |
| 2002/0177789 | A1 | 11/2002 | Ferry et al. |
| 2003/0149422 | A1 | 8/2003 | Muller |
| 2003/0163085 | A1 | 8/2003 | Tanner et al. |
| 2003/0199817 | A1 | 10/2003 | Thompson et al. |
| 2003/0201058 | A1 | 10/2003 | Banas et al. |
| 2003/0230822 | A1 | 12/2003 | Bartholomew |
| 2003/0230823 | A1 | 12/2003 | Bartholomew |
| 2003/0236493 | A1 | 12/2003 | Mauch |
| 2004/0010243 | A1 | 1/2004 | Klint |
| 2004/0097881 | A1 | 5/2004 | Brustad et al. |
| 2004/0215109 | A1 | 10/2004 | Pingleton et al. |
| 2005/0096590 | A1 | 5/2005 | Gullickson et al. |
| 2005/0131387 | A1 | 6/2005 | Pursley |
| 2005/0159728 | A1 | 7/2005 | Armour et al. |
| 2005/0165366 | A1 * | 7/2005 | Brustad et al. .................. 604/264 |
| 2005/0197623 | A1 | 9/2005 | Leeflang et al. |
| 2005/0277875 | A1 | 12/2005 | Selkee |
| 2005/0288627 | A1 | 12/2005 | Mogul |
| 2005/0288656 | A1 | 12/2005 | Koerner et al. |
| 2011/0005661 | A1 | 1/2011 | Brustad et al. |
| 2011/0066105 | A1 | 3/2011 | Hart et al. |

FOREIGN PATENT DOCUMENTS

| | | |
|---|---|---|
| EP | 0463611 A2 * | 1/1992 |
| EP | 0 605 796 A2 | 7/1994 |
| JP | 405038325 A | 2/1993 |
| WO | WO 97/10749 A | 3/1997 |
| WO | WO 00/25849 A | 5/2000 |
| WO | WO 03/015638 A | 2/2003 |

OTHER PUBLICATIONS

European Patent Office, Supplementary European Search Report for European Patent Application No. EP 07 78 3946 dated Feb. 20, 2012.

International Searching Authority, International Search Report and Written Opinion for PCT/US04/13118, mailed Mar. 8, 2006, entitled Steerable Kink Resistant Sheath.

European Patent Office, Supplementary European Search Report for Application No. EP 04 75 0825, based on International Application No. PCT/US2004/013118, dated Oct. 2, 2006.

The International Bureau of WIPO, International Preliminary Report on Patentability for International Application No. PCT/US /2004/013118, dated Mar. 27, 2006, entitled Steerable Kink Resistant Sheath.

International Search Report and Written Opinion of the International Searching Authority for International Application No. PCT/US2005/001129, mailed Nov. 23, 2005.

International Bureau of WIPO, International Preliminary Report on Patentability for International Application No. PCT/US/2005/001129 dated Jul. 31, 2006.

International Bureau of WIPO, International Preliminary Report on Patentnability for International Application No. PCT/US07/69282 dated Nov. 18, 2008.

* cited by examiner

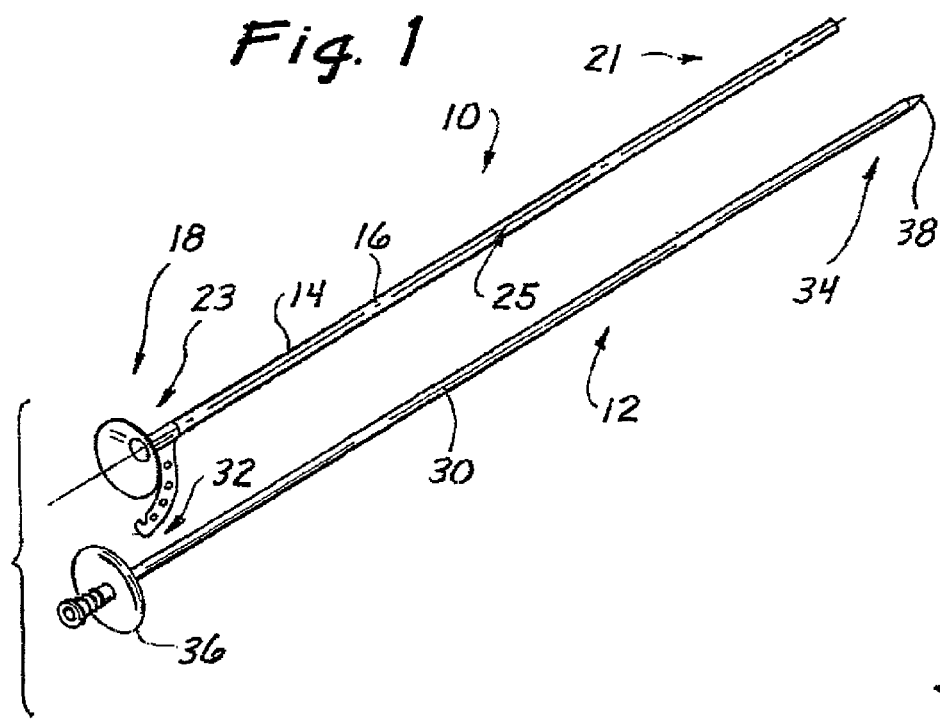

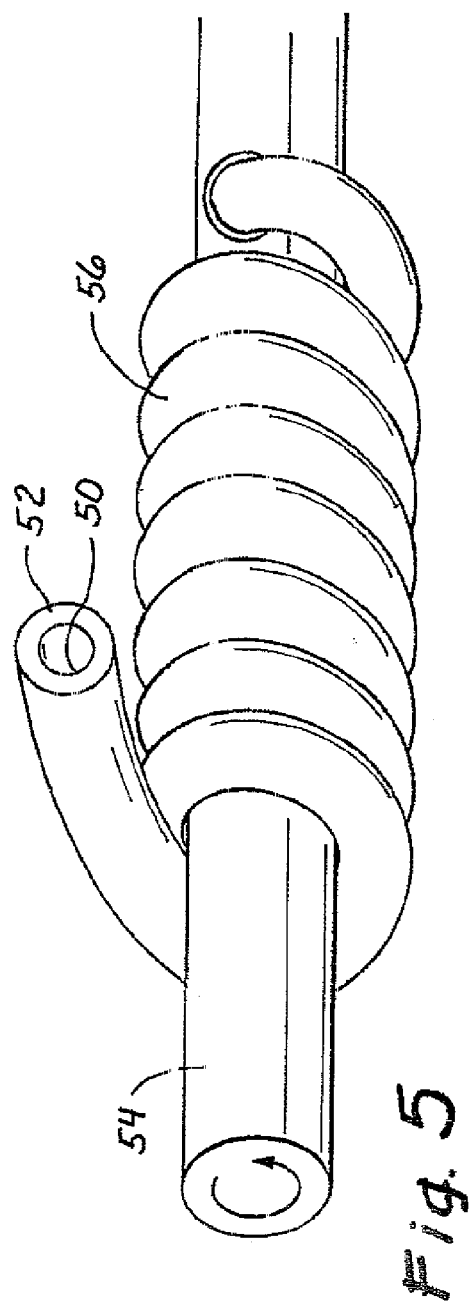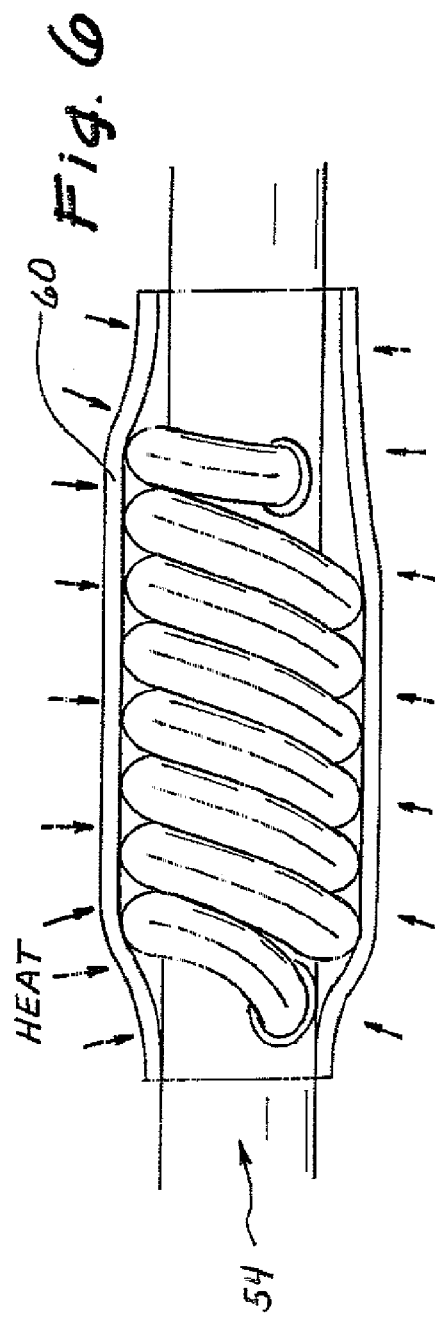

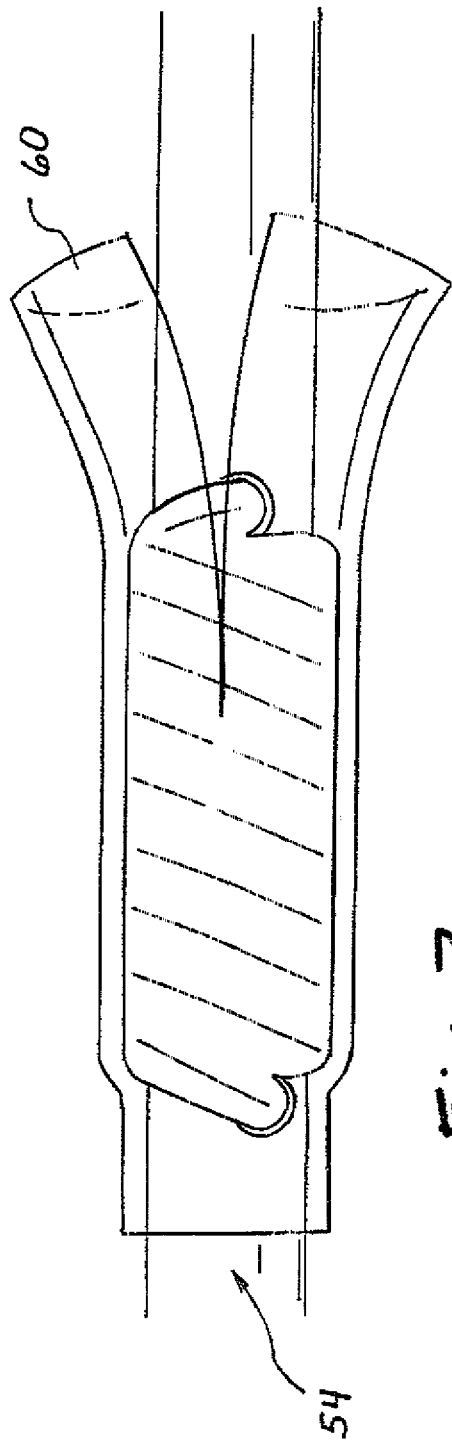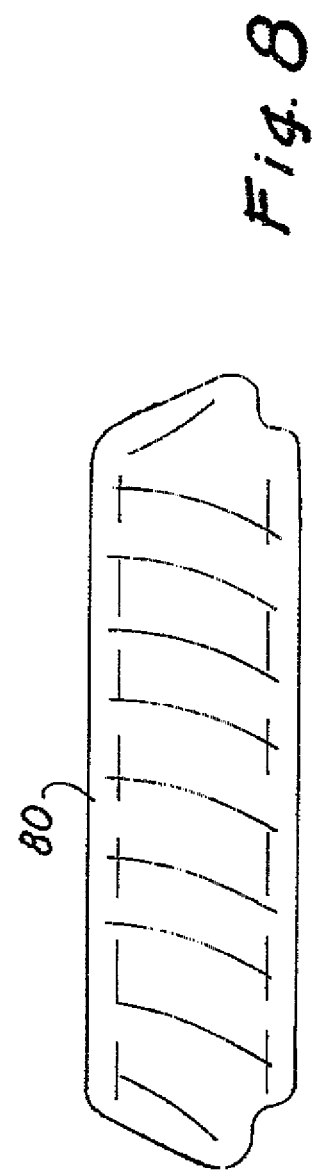

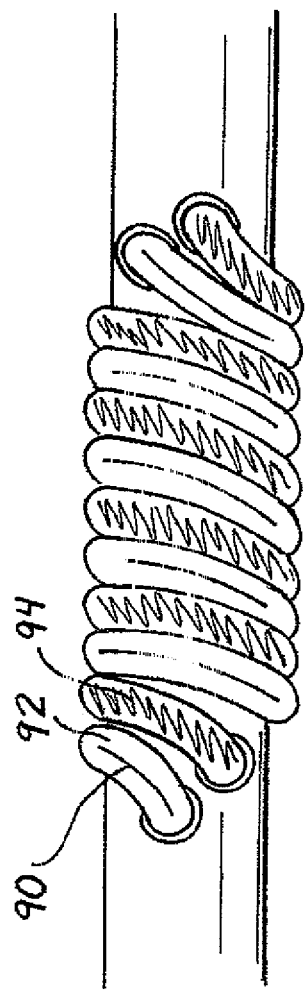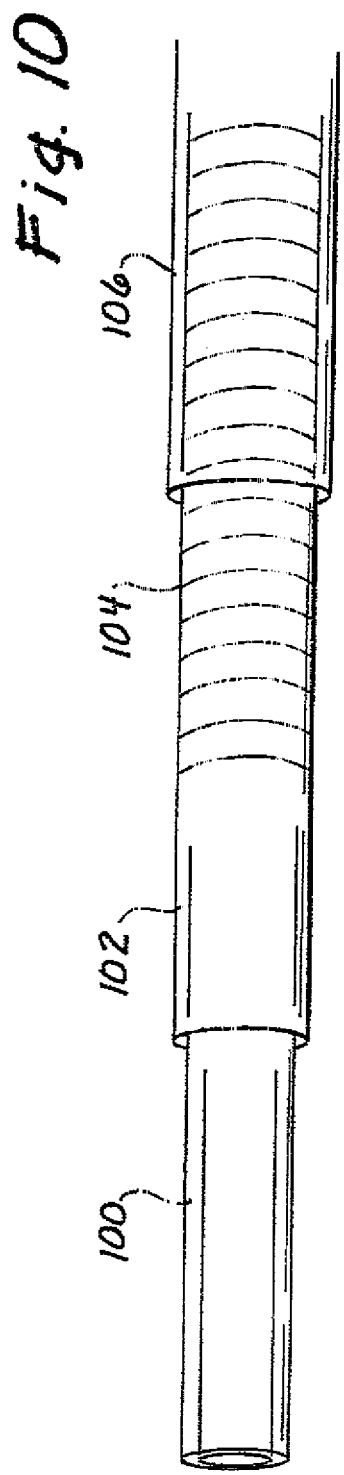

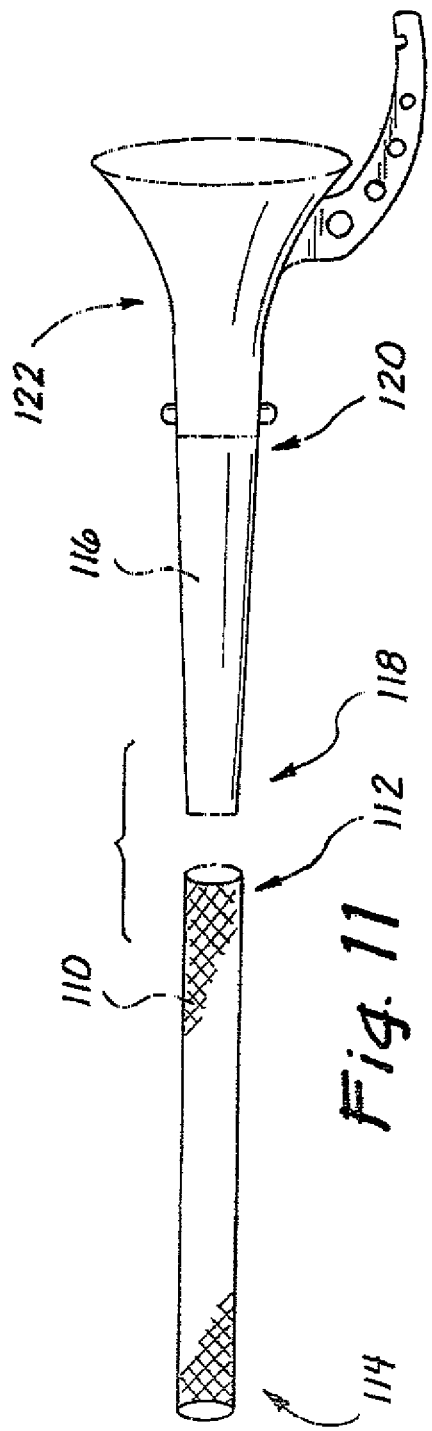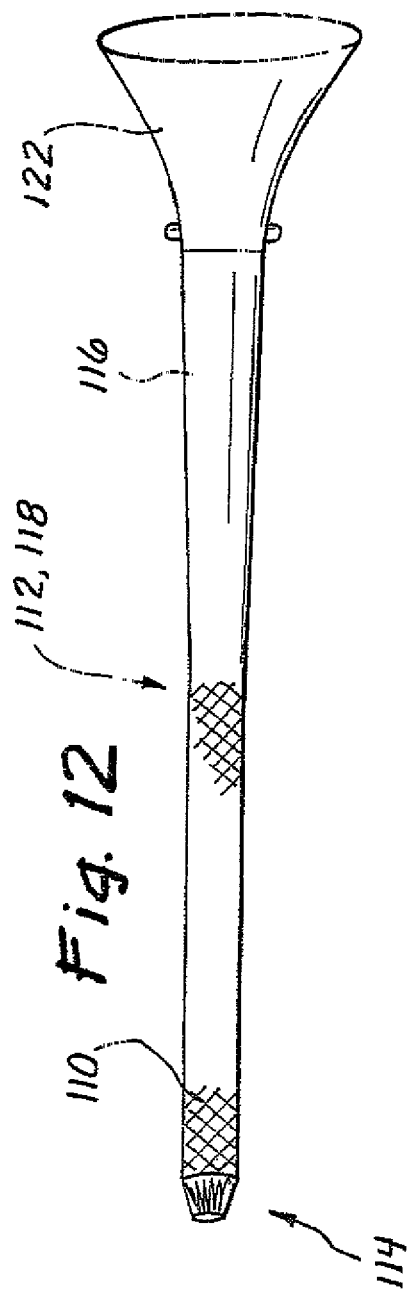

METHOD OF MAKING MEDICAL TUBING HAVING VARIABLE CHARACTERISTICS USING THERMAL WINDING

CROSS-REFERENCE TO RELATED APPLICATION

This application claims benefit of U.S. Provisional Application No. 60/747,644, filed May 18, 2006, and is a continuation-in-part of U.S. patent application Ser. No. 10/766,138, filed Jan. 28, 2004, and a continuation-in-part of U.S. patent application Ser. No. 11/319,870, filed Dec. 28, 2005, which is a division of U.S. patent application Ser. No. 10/298,116, filed Nov. 15, 2002, now U.S. Pat. No. 7,005,029, the entire disclosures of which are hereby incorporated by reference as if set forth in full herein.

FIELD OF THE INVENTION

This invention generally relates to novel methods for manufacturing medical devices, more specifically, medical tubing adapted for insertion into a body tissue or cavity and having variable characteristics.

BACKGROUND

Medical tubing includes tubing used as catheters, drain tubes, access ports, endoscope bodies and the like. The requirements for each type of medical tubing will depend on its use. In particular, a specific length of medical tubing may vary depending on each application. For example, a specific length of medical tubing may need to be very flexible and yet pushable, or it may need to be thin-walled and yet kink-resistant. In addition, the tubing may need to exhibit these properties in only specific regions.

Most medical tubing is extruded from a single plastic material in a continuous forming process. Certain characteristics or variations may be imparted to the extruded tubing by altering the speed or the tension of the extruded material as it exits and cools from the extrusion machine. However, the variations are limited by the fact that a single material is extruded. Recent advances in extrusion technology have allowed the co-extrusion of multiple materials. This provides some usable variations in extruded tubing. Nevertheless, this is still a linear process and is still limited by the continuous flow of the extruded materials.

Accordingly, there is a need for medical tubing having a length with variable characteristics and a method of making the tubing such that variations can occur along the length of the manufactured tubing. For instance, a length of the tubing may be rigid for a length, becomes flexible for a length and then becomes rigid again for another length. It is also desirable to have large variations in the diameter of the tubing. In another application, there may be a need for a tube that is extremely kink-resistant in a specific region. Kink-resistance with very thin walls is not obtainable through the current extrusion processes.

SUMMARY

The present invention is directed to a method of manufacturing a kink-resistant tube wherein a coated wire is wound around a mandrel while simultaneously being heating to melt the coating, for example, a thermoplastic, around the wound wire to form a tube. The wire may be a metal or a nonmetal; the wire may also be a braided material. In one embodiment, more than one coated wire is wound around the mandrel.

Several heat sources may be used to melt the coating as the coated wire in wound; in one embodiment, the heat source comprises one or more hot air gun(s).

If desired, the tube can be provided with a smooth surface by, in one embodiment, applying a roller, optionally heated, against the tube as the thermoplastic is melted. The tension of the roller against the tube can be controlled by, for example, a tension spring. In another embodiment, the wire is passed through a die or split die following melting of the coating to smooth the surface. Alternatively, the tube can be provided with a textured surface by applying a textured roller against the tube.

In one embodiment, the mandrel has a circular cross-section, while in other embodiments at least a portion of the mandrel has a noncircular cross-section. The mandrel may have a constant or a variable diameter along its length.

Tubes of varying flexibility can be manufactured by, for example, winding the coated wire around the mandrel with a variable pitch.

In one embodiment, the invention is directed to a method of manufacturing a kink-resistant tube comprises the steps of placing a mandrel between two spindles of a winding machine; winding a co-extruded wire comprising a core coated in a thermoplastic polymer around the mandrel a few times; attaching the end of the co-extruded wire to the spindle; starting the winding machine and winding the co-extruded wire over the mandrel while applying heat from at least one hot air gun to melt the thermoplastic polymer as it is wound around the mandrel, with a roller trailing the hot air gun to smooth the surface of the melted thermoplastic polymer, to thereby form a tube; when the winding is complete, cutting the co-extruded wire close to the mandrel and removing the mandrel with the tube from the winding machine; and removing the tube from the mandrel.

The present invention is also directed to a method for manufacturing a coated guidewire, wherein a coated wire is wound around a core wire while simultaneously heating the coated wire, to thereby melt the coating around the two wires (the core wire and the wire wound around it).

In one embodiment, the invention is directed to a method for manufacturing a coated guidewire, comprising the steps of placing a core wire between two spindles of a winding machine; winding a co-extruded wire comprising a metal wire coated in a thermoplastic polymer around the core wire a few times; attaching the end of the co-extruded wire to the spindle; starting the winding machine and winding the co-extruded wire over the core wire while applying heat to melt the thermoplastic polymer as it is wound around the core wire to thereby produce a coated guidewire; when the winding is complete, cutting the co-extruded wire close to the core wire and removing the coated guidewire from the winding machine.

The present invention is also directed to kink-resistant tubes, usable in a wide variety of applications, and to coated guidewires, made according to the inventive methods described herein.

DESCRIPTION OF THE DRAWINGS

FIG. 1 is a perspective view illustrating a sheath having a handle with an obturator having a releasable mechanism adapted for use with the handle of the sheath;

FIG. 2 is a perspective view illustrating the obturator operatively disposed within the sheath;

FIG. 5 illustrates a coated wire being wrapped around a mandrel forming a reinforcement spring in a process of manufacturing a kink-resistant sheath in accordance with an embodiment of the invention;

FIG. 6 illustrates the heating process of the wound coated wire using a shrink tube in a process of manufacturing a kink-resistant sheath of the invention;

FIG. 7 illustrates the removal of the shrink tube after heating of the wound coated wire in a process of manufacturing a kink-resistant sheath of the invention;

FIG. 8 illustrates a coating of the spring reinforcement in a dipping process in accordance with another embodiment of the invention;

FIG. 9 illustrates a coated wire being alternatively wound around a mandrel with a filament comprising a material different from the coating of the wire;

FIG. 10 illustrates a mandrel being used in an extrusion process in accordance with another embodiment of the invention;

FIG. 11 illustrates a side view of a braid and a tube prior to being fused in accordance with another embodiment of the kink-resistant sheath of the invention;

FIG. 12 illustrates fusing of the proximal portion of the braid and the distal portion of the tube;

DETAILED DESCRIPTION

Figure 3:
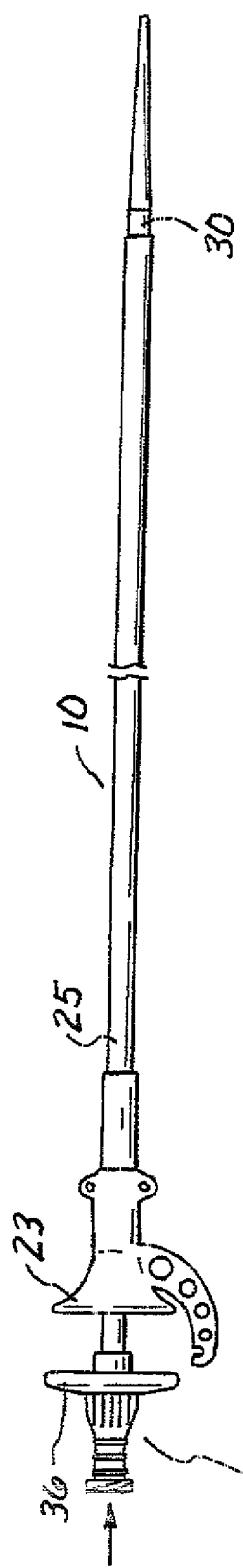
FIG. 3 is a side view illustrating the obturator with a cap operatively disposed within the sheath with the handle.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the structures and/or methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

An access sheath is illustrated in FIG. 1 and is designated generally by reference numeral 10. In FIG. 1, the sheath 10 is illustrated in combination with a separate, but associated, dilator or obturator 12. The sheath 10 has the general configuration of an elongate tube 14 having an axis 16 which extends between a proximal end 18 and a distal end 21. A handle 23 is disposed at the proximal end 18 of the tube 14 and provides access into a working channel 25 of the tube 14. The handle 23 is formed as a radial enlargement having a distally-facing surface and a proximally-facing surface. The distally-facing surface has a generally concave configuration which provides a gradual enlargement inhibiting migration of the sheath 10 into a body cavity such as the ureter. The concave configuration is sized to receive adjacent fingers of a user's hand disposed in its natural position, in order to facilitate the stationary orientation of the sheath 10. The proximal-facing surface has a generally convex configuration providing for an increased funneling of an instrument as it is inserted into the working channel 25 of sheath 10. Thus, the handle 23 has the general configuration of the bell of a horn. This configuration is not only ergonomically comfortable, but also highly practical in addressing the problems of migration, as well as instrument insertion and removal.

The obturator 12 will typically have the configuration of an elongate rod 30 extending between a proximal end 32 and a distal end 34. In a preferred embodiment of the invention, a releasable mechanism 36 shaped like a cap is disposed at the proximal end 32 and a tapered tip 38 is formed at the distal end 34. The obturator 12 is adapted to be inserted into the working channel 25 of sheath 10 with the releasable mechanism 36 extending proximally of the sheath 10, and the distal end 34 extending distally of the sheath 10. This operative position of the obturator 12 within the sheath 10 is illustrated in the assembled view of FIG. 2. A side view of the assembled combination is illustrated in FIG. 3. The releasable mechanism 36 is provided to removably attach the obturator 12 to the handle 23 of sheath 10.

Figure 4:
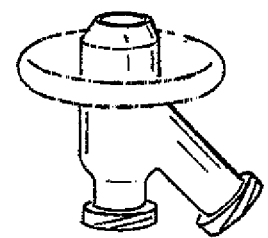
FIG. 4 illustrates another embodiment of a releasable mechanism having multiple openings.

When locked in place with the releasable mechanism 36, the obturator 12 and sheath 10 can then be passed as a single unit over an instrument such as a guidewire. This arrangement precludes inadvertent advancement of the sheath 10 in front of the obturator 12, which could greatly impede proper passage of the sheath through a body cavity such as the ureter. The releasable mechanism 36 is sized and shaped to fit the handle 23. Once the obturator/sheath combination has been advanced to the desired position in the body cavity, the obturator 12 can be removed from the sheath 10 by removing the releasable mechanism 36. Another surgical instrument having a releasable mechanism disposed at its proximal end may then be introduced into the sheath 10, or a separate releasable mechanism may be attached to the handle 23 to prevent passage of fluids or instrumentation. It is appreciated that the releasable mechanism 36 may have different configurations including a snap-on cap as illustrated in FIGS. 1-4, a twist-on cap and any foreseeable releasable mechanism that fits the handle 23 of sheath 10. It is further appreciated that the releasable mechanism may include additional openings such as Luerlock connectors or sidearms providing additional working channels into the sheath as illustrated in FIG. 4.

Another aspect of the invention is the tube 14 may be formed with a spring coil to provide a high degree of kink resistance. As discussed above, there are many advantages to a kink-resistant design of the access sheath such as safety and easy passage of instrumentation U.S. Pat. No. 5,380,304 (the '304 patent) and U.S. Pat. No. 5,700,253 (the '253 patent) disclose one such design by reinforcing the elongate tube of the access sheath with a coil.

The current methods of fabricating kink-resistant access sheaths, however, are time-consuming, costly and do not provide good yields. Moreover, the fabricated access sheaths do not have a good shelf life. This is because the current manufacturing processes include several challenges. In one example, a current manufacturing process undergoes a dipping process where (1) a mandrel is first dipped in a plastic or PVC material, (2) a wire is then wrapped or wound around the dipped mandrel, and (3) the assembly is then dipped again in the plastic or PVC material multiple times to form the access sheath. While this is a feasible method of producing a kink-resistant access sheath, it is time consuming, costly and produces undesirable yields. The present invention, accordingly, provides alternative methods of manufacturing kink-resistant access sheaths that are more efficient, less costly and provide better yields and improved shelf life.

In a first method of the invention as illustrated in FIG. 5, a wire 50 is initially coated with a plastic material 52, e.g., in a coextrusion process; the coated wire 50 is then wrapped or wound on a straight or tapered mandrel 54 forming a desired reinforcement spring 56 (i.e., forming a profile of the resultant tube); after wrapping, the wound coated wire is heated until the plastic material 52 melts and bonds the windings to form the resultant tube or sheath; and once cooled, the sheath is removed from the mandrel 54. It should be noted that the wound coated wire is heated until the plastic material 52 is formed above, below and in between the wire 50.

The wire/plastic coextrusion may be round, have straight edges that can be laid adjacent to each other when winding or have interlocking shapes. The wound coated wire may be heated in one of several ways including: (i) capturing the windings within a shrink tube 60 as illustrated in. FIG. 6 and heating until the shrink tube 60 encapsulates all the windings and the sheath is formed; (ii) using a mold to compress the windings and heating the windings until the sheath is formed; and (iii) spinning the coextruded wire around a mandrel, securing both ends of the wire to the mandrel and rotating the mandrel with the coextruded wire in an oven to heat, the constant rotation of the mandrel obviating the need for a sleeve.

If used, the heat shrink tube or mold is then cut or removed from the sheath as illustrated in FIG. 7. That is, after the plastic material such as polyurethane has melted together to form the sheath with spring reinforcement, the shrink tube is cut away and the mandrel is removed.

It is appreciated that the plastic material could be polyurethane, a thermoplastic, a thermoset or any plastic material having hard and/or soft durometer. It is further appreciated that the coated wire could be wound onto the mandrel in a multifilar fashion with materials having alternating durometers as illustrated in FIG. 9. In this embodiment, a wire 90 coated with a more rigid material 92 is alternatively wound with a filament 94 comprising a softer material. The wound coated wire would perform like a spring coil while the softer filament would behave as the more compliant body of the tube allowing kink-resistant bending and twisting. The difference in the durometer of the two materials does not need to be substantial.

The following is an example of a process described above for making thin-walled tubes of the invention:

(1) First, a mandrel of steel is machined to match the internal diameter or shape of the intended tube;

(2) Second, a stainless steel wire, e.g., of about 0.006" in diameter has a layer of polyurethane co-extruded onto it with a resulting diameter of about 0.020";

(3) The co-extruded wire is close wound around the length of the mandrel and the ends are secured such that the resultant coil will not unwind;

(4) Fourth, a silicone tube with an inner diameter (I.D.) less than that of the wound coil outer diameter (O.D.) is placed over the entire assembly such that it completely covers the wound coil;

(5) Fifth, the assembly is placed in an oven at approximately 180° C. for 15 to 30 minutes (this is for Pellethane; other plastics require different parameters);

(6) Sixth, the assembly is removed from the oven and cooled. The silicone sheath is removed once the assembly has cooled; and (7) Seventh, the wound coil is removed from the mandrel This process results in a tube with walls of about 0.015" in thickness and a reinforced coil of stainless wire embedded in it. The tube is virtually un-kinkable and has very smooth inner and outer diameter surfaces. In addition, the mandrel can be tapered to provide a tube with variable diameters from one end to the other. In other examples, physical properties of the resulting tube can be adjusted by varying the diameter of the wire, the diameter of the co-extruded plastic, the type and properties of the wire and plastic such as chemical composition and hardness. The tolerance that can be held on the I.D. of the tube is very high and on the order of 0.001" or less. The tolerance on the O.D. is comparable. The range of diameters for this process is quite large. Prototypes have been made from 0.026" I.D. to 0.75" I.D. and with wires from 0.004" diameter to 0.008" inch diameter.

It should be noted that two or more different types of wire/plastic extrusions can be wound together and the wire is not a requirement for this process to work. This process would be useful for molding thin wall tubes to dimensions that are not practical or obtainable by extrusion or traditional molding. Mandrels do not need to be round and could combine both round and non-round shapes on the same mandrel.

In another aspect of the invention as illustrated in FIG. 10, a mandrel 100 is used as part of an extrusion process. In particular, the mandrel 100 is coated with a first layer 102 that would be the resultant internal surface of the tube. A spring reinforcement 104 would then be placed over the first layer 102, and then an outer layer 106 would be extruded over the spring reinforcement 104. An advantage of this embodiment is the resultant tube is not being contoured based on the process itself. As a result, a contoured section could be easily added to an end of the tube providing improved movement of the tube. The addition of the contoured section could be done by either insert-molding, over-molding or melding (fusing) of the contoured section to the tube. It is appreciated that the spring reinforcement 104 could be a pre-wound wire placed around the first layer 102 or a wire wrapped around the first layer 102. It is further appreciated that the gaps between the wires are filled and that the final tube has little or no voids or air bubbles.

In another embodiment of the invention as illustrated in FIG. 8, another coating or outside layer 80 could be placed over the spring reinforcement by means of a dipping process. In particular, after the mandrel has been coated and the spring reinforcement has been placed or wrapped, the assembly is then dipped in a solvent based solution to form the outer layer 80 onto the tube or sheath. It is appreciated that the final coating could be formed on the resultant tube or sheath using a dipping process either in place of or in addition to the outer layer formed by extrusion. In other words, the final coating could be extruded and/or dipped. It is preferable that the final coating is impervious. An advantage of this embodiment is it allows a layer of a desired material to be formed on the surface of the resultant tube. In yet another embodiment of the invention, a thin flat sheet of polyurethane having a specific width and thickness may be wrapped around the mandrel as a coating. An advantage of this embodiment is it forms an even and smooth coating and it gives some control over the thickness of the coating.

As discussed above, the wire reinforcement could be pre-wound or wound during each of the above processes. Moreover, the material of the wire, the hardness of the wire, the pitch of the windings and the shape of the wire could vary depending on the surgical application of the tube or sheath. For example, the wire may comprise a metallic and/or plastic material. The cross-section of the wire may be round, flat, hexagonal or any other shape that facilitates interlocking of the windings. The use of harder or softer durometer materials is also important as to the inner or outer layer of the tube. Another configuration of the invention uses double reversed springs.

In another aspect of the invention, a braid such as a polyester braid may be used instead of or in addition to the coil spring to form a kink-resistant sheath as generally illustrated in FIGS. 11-15. The braid may comprise of woven fibers made of plastic, metal or any combination of plastics and metals. In one configuration, a spring of length x is placed over a braid having a length of approximately 2x, the excess braid is then inverted over the spring to form a sheath having two layers of braid surrounding the spring. It is appreciated that the braid may be heat fused to prevent axial stretching. Furthermore, the braid may be insert molded, fused or bonded onto the sheath.

Figure 13:
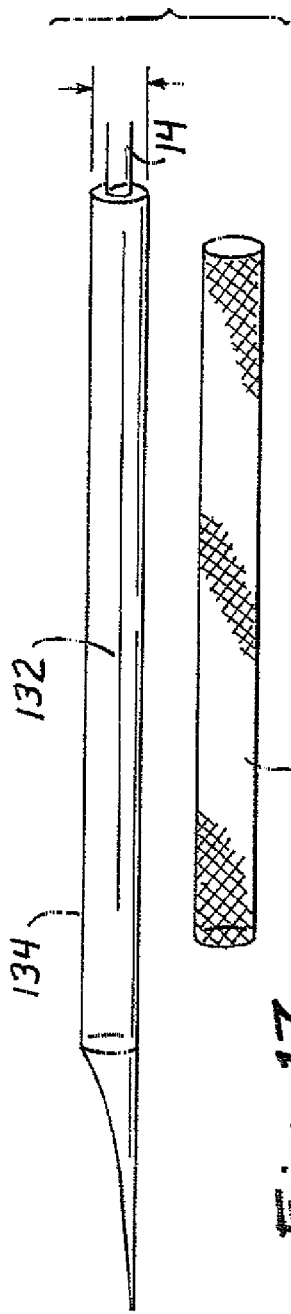
FIG. 13 illustrates a side view of a braid and a tube extruded with a plastic material prior to being fused.
Figure 14:
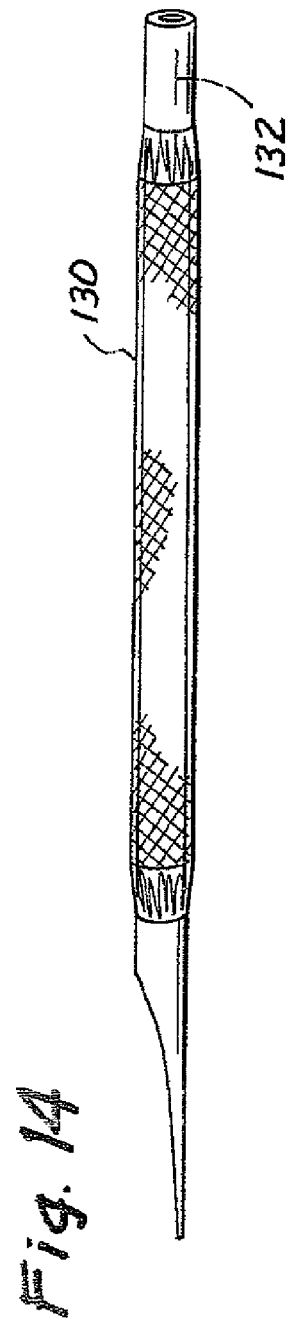
FIG. 14 illustrates fusing of the braid and the tube.
Figure 15:
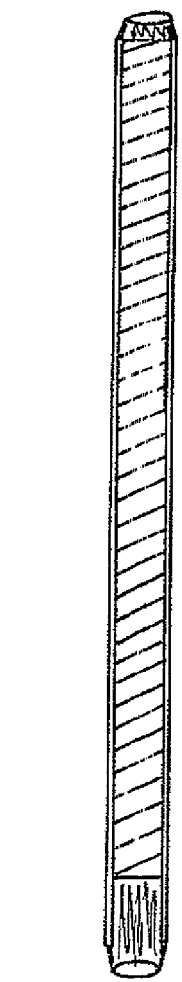
FIG. 15 illustrates a coating of the fused braid and tube with a solvent based solution.

FIG. 11 illustrates an exemplary braid 110 having a proximal portion 112 and a distal portion 114 with a tube 116 having a distal portion 118 and a proximal portion 120 attached to a handle 122 FIG. 12 illustrates the fusing of the proximal portion 112 of braid 110 with the distal portion 118 of tube 116. FIG. 12 further illustrates that the distal portion 114 of braid 110 may be insert or over-molded in a partially deployed condition, fully deployed condition or in a straight condition. FIG. 13 illustrates a braid 130 and a tube 132 extruded with a plastic material 134 prior to fusing. FIG. 14 illustrates the fusing of the braid 130 and tube 132. Finally, FIG. 15 illustrates the coating of the braid 130 and tube 132 with a solvent based solution either by dipping or extrusion.

The present invention also contemplates the use of mandrels or forms that may have curves or other useful forms or shapes that fit various uses. For instance, guiding catheters may be constructed that have pre-formed curvatures for accessing specific anatomical regions of a body. Mandrels or forms may include collapsible, inflatable, dissolvable or the like that allow the resultant tubular body to have variations in diameter and lumen size. As an example, a mandrel or form may be constructed of an electrically dissolvable epoxy resin. The mandrel or form retains its shape until an electrical impulse is applied. The material separates upon application of electrical energy leaving a complex lumen shape within the tubular body.

The main requirement is that the resultant shape be capable of being removed from the mandrel once the heat cycle is finished. With unusual shapes this could be accomplished with split mandrels and sacrificial mandrels that could be removed by dissolving in acid by way of example.

The following is still another example of a process for making thin-walled tubes of the invention using thermal winding, a process in which co-extruded wire coated in a thermoplastic is simultaneously wound around a mandrel and heated to melt the plastic.

First, a mandrel is placed between the spindles/chucks of a winding machine, such as the Continuous Winder, manufactured by MCS Control Supply, and the chucks tightened down on the mandrel. The mandrel can be made of a variety of materials, including but not limited to stainless steel, nitinol or PFET coated aluminum/steel.

Second, a co-extruded wire comprising a metal core (the cross section may vary in shape, i.e., round, oval, star-shaped, polygonal, rectangular, triangular, square, etc.) coated in a thermoplastic polymer is wrapped around the mandrel about three to four times, and the end of the co-extruded wire attached to the chuck/spindle.

Third, the winding machine is started, winding the co-extruded wire over the mandrel while applying heat from one or more hot air gun(s) or other heat source(s) to melt the plastic as it is wound around the mandrel, with a roller, preferably heated, trailing the hot air gun to smooth the surface of the melted plastic. Preferably, the roller has an adjustable spring tension device so that the amount of pressure applied to the plastic coated wire may be adjusted. The mandrel may need to be stabilized during winding, depending on the diameter and the length of the mandrel. By stabilizing the mandrel as it is spinning, a more consist final product may be achieved.

Fourth, when the winding is complete, the co-extruded wire is cut close to the mandrel, the head is returned to the start position, and the mandrel is removed from the winding machine by loosing the chucks securing the mandrel.

Fifth, the tube is removed from the mandrel. As will be appreciated, melting the plastic around a co-extruded wire as it is wound around a mandrel will produce a tube having a wire spring embedded in the melted plastic. To remove this tube from the mandrel, one end of the mandrel is placed into a vice and secured; the plastic tube is then twisted in the direction that will cause the spring to expand, increasing the inner diameter of the tube and facilitating its removal. To ensure that the ends of the tube are clean, a razor or other cutting device may be used to trim both ends of the tube.

Figure 16:
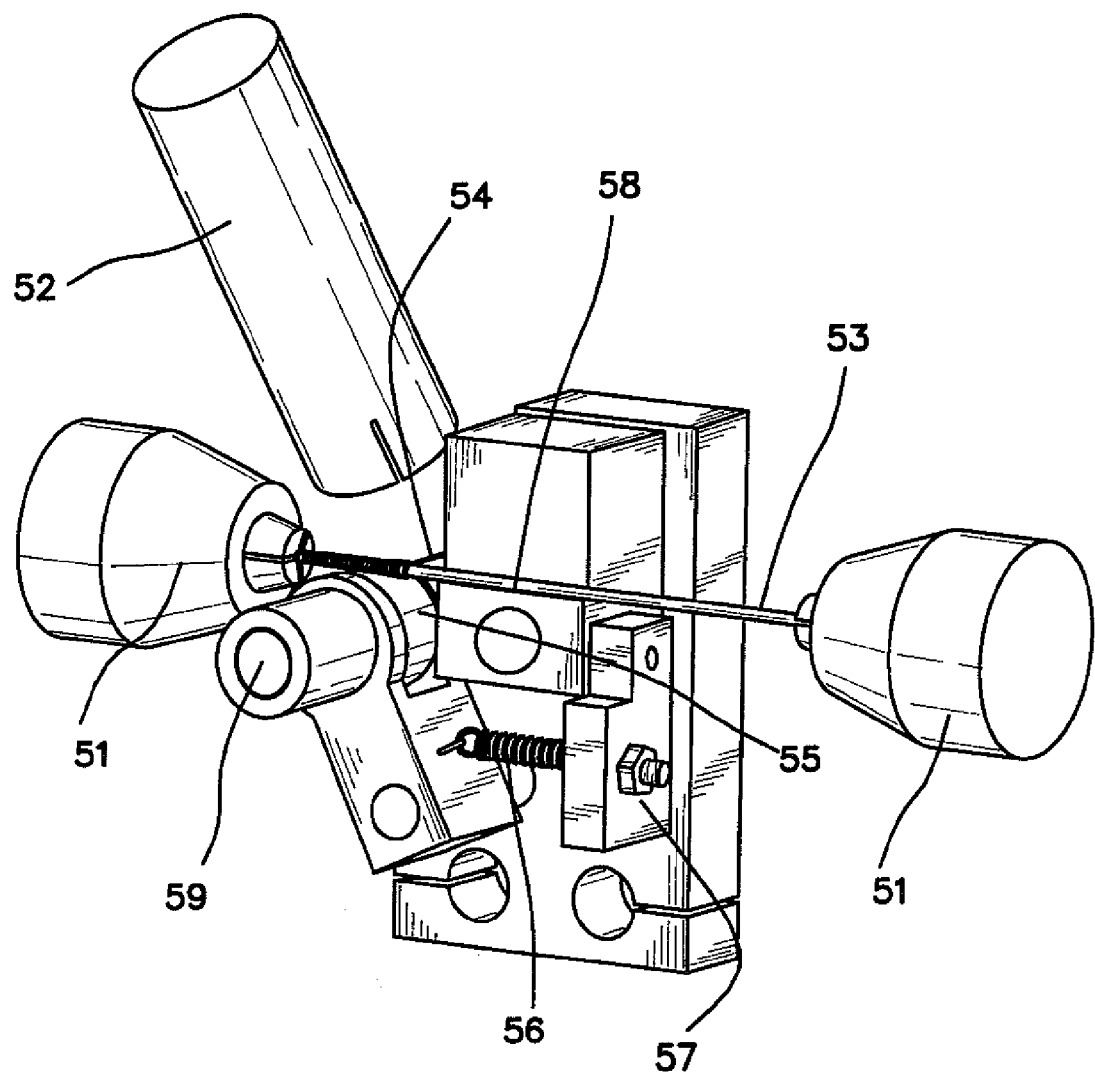
FIG. 16 shows an apparatus used for manufacturing variable characteristic tubes by thermal winding.

An apparatus useful in practicing the above method is shown in FIG. 16. The apparatus includes a pair of spindles 51 with a mandrel 53 secured between them. A hot air gun 52 is directed at one end of the mandrel, where a plastic-coated wire 54 is being wrapped around the mandrel. A roller 55, with a cartridge heater 59, presses against the melted plastic to smooth the surface of the tube, the pressure of the roller against the tube adjusted by a tension spring 56 attached to a nut and bolt 57. The mandrel may be stabilized by a shelf 58 on the winding apparatus.

Figure 17:
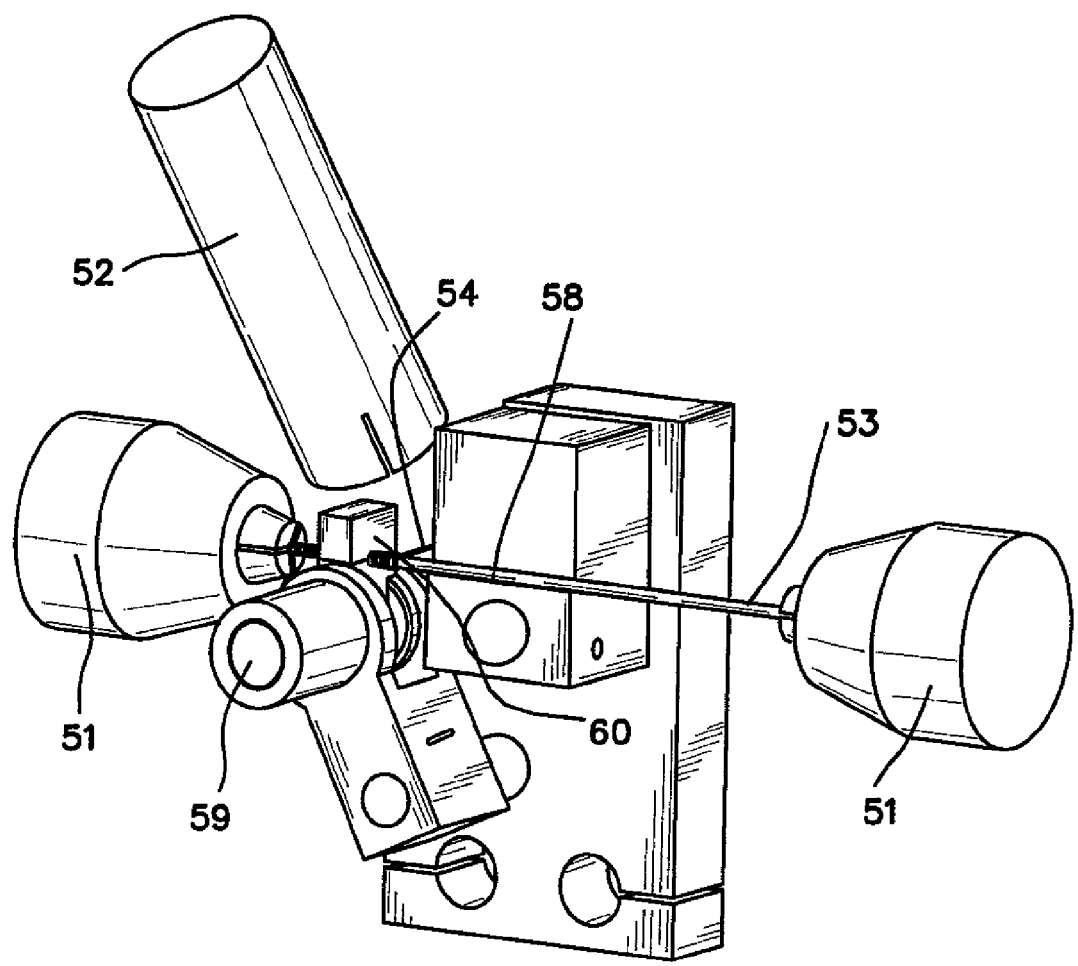
FIG. 17 shows a variation of the apparatus of FIG. 16, using a die or split die instead of a heated roller.

A variation of this apparatus is shown in FIG. 17, in which a die or split die 60 is used instead of the heated roller. In this embodiment, the coextruded wire 54 is wound around the mandrel 53, heated by an air gun 52 (or other heat source) then passed through the die or split die 60 to smooth the plastic surface of the tube.

Figure 18:
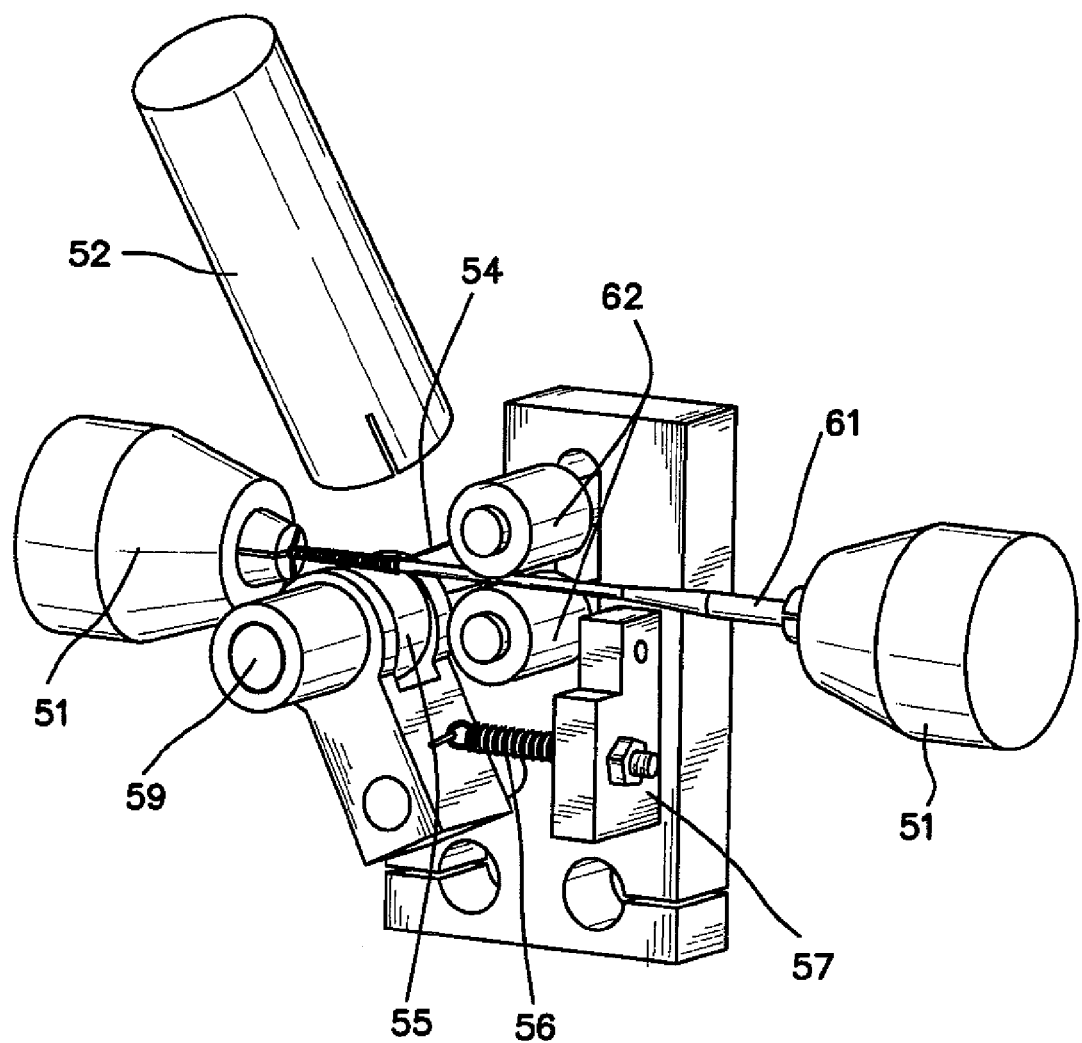
FIG. 18 shows a variation of the apparatus of FIG. 16, having a variable diameter mandrel used to produce tubes having a tapered section by thermal winding.

As shown in FIG. 18, a tapered tube or a tube with a tapered tube section can also be produced using this apparatus and process. Here, a tapered mandrel 61 is used, with a floating mandrel stabilizer 62 providing stability along the entire length of the mandrel as it moves relative to the winding machine.

Figure 19:
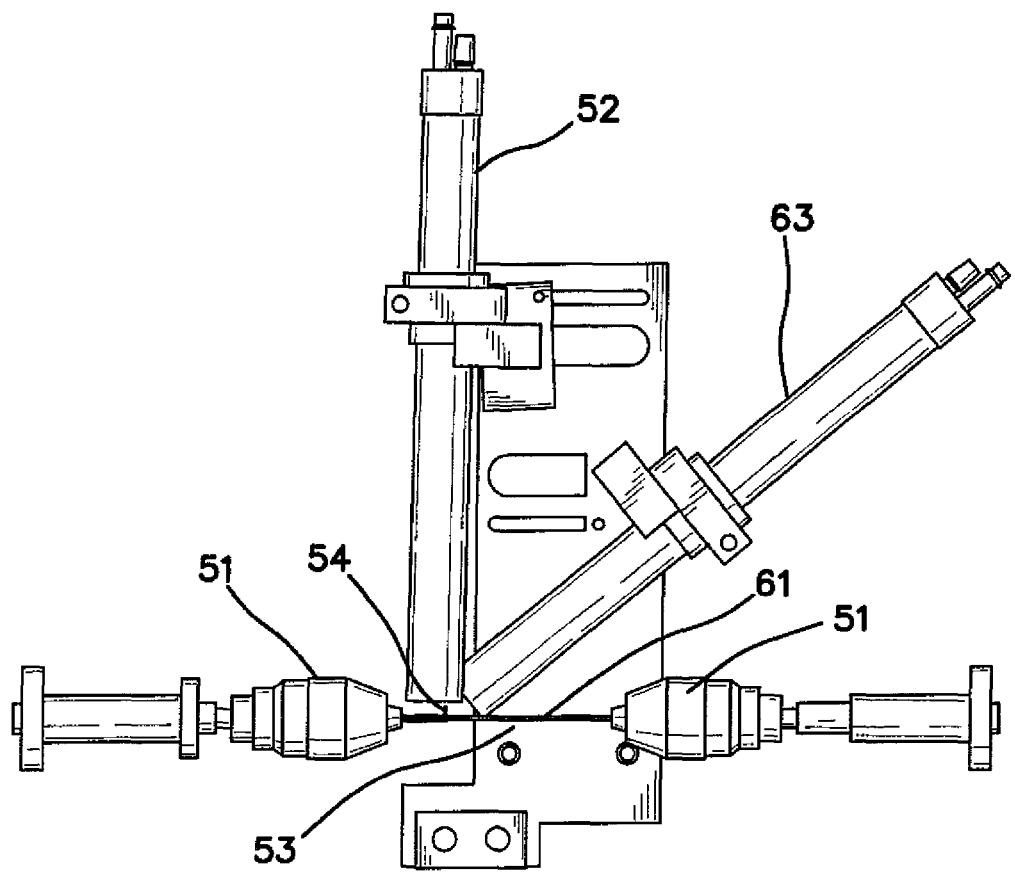
FIG. 19 shows a variation of the apparatus of FIG. 16 having a second hot air gun.

Another embodiment of this apparatus is shown in FIG. 19, where a second hot air gun 63 is provided.

The speed of the winding machine and the temperatures of the hot air and the heated roller are dependant on the material and diameter of the co-extruded wire and the diameter of the mandrel. For example, higher heat or heat residence time is required for larger diameter mandrels or larger diameter wires. The angular velocity of the mandrel and the mass of the mandrel itself both affect the performance of the process. Larger mandrel diameters require lower rotational speeds to increase the residence time of the hot air at any one point along the winding process. Additionally, the larger diameter mandrels require increased heating in order to overcome the mass of the larger mandrel, as the mandrel must be properly heated in order to properly form the inner surface of the tube. This additional heat can be achieved by either increasing the hot air temperature, slowing down the speed of the rotation, or a combination of both.

As will be appreciated, the above thermal winding process has several advantages, including:

Reduced manufacturing time, cost, and complexity.

Ability to quickly and easily modify the product by changing the pitch of the wire as it is wound. For example, a steeper pitch will produce a more flexible product while a shallower and more compact winding will produce a stiffer product.

Ability to produce a tube with variable properties along its length by changing the pitch of the wire as it is wound, making the tube stiffer, or more flexible, in different areas of a "single-piece" tube.

For example, a tube was made by this process using a 0.015" diameter co-extruded wire (with a wire diameter of 0.005"), altering the pitch of the wire from 0.005" to 0.015" along the length of the tube. Greater wire pitches can be achieved by varying the winding speed, temperature, and the cross-sectional shape of both the wire and co-extrusion. The pitch can remain constant along the tube, producing a tube with uniform properties, or the tube can be made having several different pitches along its length. For example, the first 1" of the tube could have pitch of 0.010", the next 3" a pitch 0.007", the next 4" a pitch of 0.015", the next 3" a pitch of 0.007", and the final I" a pitch of 010". By doing so, the end product achieves varying physical properties (i.e., stiffness, kink resistance, flexibility, compressibility, and strength) within one consistent body.

The thermal winding process described above can be applied to a guide wire or other device that only requires an exterior surface where the mandrel is not removed. For example, using a wire as the mandrel, plastic can be extruded and melted onto the wire to produce a coated guidewire, for example.

When the thermal winding process is used to produce a guide wire, it may be desirable to attach a plastic tip to the guidewire thus produced. This may be done as follows:

First, a piece of tubing having an appropriate O.D., and I.D. is cut to a predetermined length and placed over the tapered core wire, butting the end of the tube up against the end of the thermal winding part of the guide wire.

Second, the tapered core wire with the tubing over it is placed into a silicone tube, making sure that the silicone extends over both ends of the tubing.

Third, the silicone tube is clamped to the thermal winding part of the guide wire, then stretched to a predetermined amount and clamped to the other end of the fixture. By tensioning the silicone tubing, a compressive force is created around the outside diameter of the thermal winding tube.

Fourth, the guide wire, fixture, silicon tube are placed in an oven at a predetermined temperature and for a predetermined time, to fuse the tubing to the end of the guide wire. Alternative sources of heat, such as a hot air gun or heated bath, can also be used.

Finally, the assembly is removed from oven and allowed to cool, and the coated guidewire is removed from the fixture and silicone tube.

Over-molding a plastic tip onto the tapered core wire is another way to accomplish the same task. A pre-manufactured tip could also be connected to the thermal winding tube using an adhesive, solvent bond, or mechanical attachment.

There are several variations of the thermal winding procedure described above, which may be used to produce tubing and coated wires with a wide range of properties. These include, but are not limited to, the following:

Using a nonmetal "wire" during the thermal winding process; for example, the wire can be made from a different polymer or a different durometer material.

The wire can be a filament of braided material.

Winding can be done in multiple passes, producing different patterns, such as cross hatch, braid, honeycomb, lattice, etc.

Plastic can be melted over a lattice on a mandrel, producing a tube that will stretch as an instrument is inserted into it.

The pattern and direction of winding can be varied.

Multiple wires can be used in the winding process.

Wires can be applied axially rather than circumferentially to provide column strength rather than hoop strength.

Wires can be applied both axially and circumferentially to provide superior hoop and column strength.

By simultaneously applying heat and wire (coated or uncoated), the wire pitch can be varied to provide variable flexibility along the length of the tube.

The thermal winding process can be modified to make flat-sheet structures (e.g. malleable organ graspers, retractors).

The roller can be textured to produce tubes with textured surfaces (e.g., to hold a hydrophilic coating better).

Different thermoplastics may be used in this process, each with a different rate of melting/cooling; amount of shrink, etc.

One can variably extend a spring over the mandrel and extrude plastic over it, melting the plastic between the coils, providing a tube with variable flexibility along length.

In addition to the above variations, the mandrel can have different cross-sectional shapes, can be tapered, or can be a spring.

Plastic can be melted during winding using a variety of methods, including heat (hot air, hot oil, etc.), chemical (which can be controlled by quick dunking into water, to precipitate the solvent out to stop the reaction), pressure, radiofrequency (RF), vibration, friction, spin welding, microwave, and induction. Heating elements can be on the mandrel, externally or internally, or a hot air gun or other external heat source can be used, or both. Heating elements can also be used on the roller.

In another embodiment, wire can be heated as it is wound around a plastic tube, to melt into tube as it winds, followed by melting the plastic surface and smoothing the surface as above.

There are also several possible methods for removing the thermally wound product from the mandrel, including:

Using a tube with harder durometer as the mandrel—at end of process, the mandrel is stretched to reduce its diameter, facilitating removal of the wound product.

The mandrel can be a compressible cone, compressed for use as mandrel, then release to spring back with reduced diameter to facilitate release of the tube from mandrel.

A dissolvable mandrel can be used along with a solvent (or heat) that will dissolve mandrel but not tube product; this allows mandrel to have variable cross-section (e.g. "table-leg" conformation)

Cold air can be used to limit shrink and facilitate removal of the produced tube.

The method of the invention may be applied in the construction of the following products, at least in part if not in whole:

AV introducers: These devices are used to gain access to blood vessels. The AV introducers of the prior art are typically fairly thick walled flouropolymer about 2-3 inches long. The AV introducers of the invention decrease wall thickness and at the same time increase kink resistance. Vascular surgeons also use longer versions of these to access various parts of the vascular system and then use these sheaths to inject various medicants or use them as a highway for the introduction and removal of instruments. These longer versions can be 70 centimeters in length or more and would benefit tremendously by the increased kink resistance and flexibility that the AV introducers of the invention would offer. More specifically, the sheath of the invention would be capable of being coated internally as well as externally with friction reducing coatings such as hydrophilic coatings as well as heperanized coatings or other medically beneficial surface treatment.

Urological sheaths: Different urological sheaths can be produced by the methods of the present invention, e.g., ureteral access sheaths, urethral and bladder access sheaths, and kidney access sheaths modified to direct a scope for various procedures.

Ureteral stents: These can be made with the process of the invention and would have the benefits of thin walls, high column strength and tremendous flexibility. The common wisdom in urology is that thin flexible stents are more comfortable for the patient but more difficult for the physician to place. Larger more rigid stents are easier to place but uncomfortable for the patient. The stent of the invention would be both small and flexible and yet easy to place due to its inherent column strength.

Trocar cannula: These can be made to be very thin walled and yet flexible (or inflexible), and can be very resistant to kinking or compressing. This may be achieved by the bonding or fusing process of the invention with a braided structure instead of a coil. In another aspect, a folded structure could be made that would allow the cannula sheath to be inserted first followed by the cannula itself.

Suction/Irrigation (S/I) tubing: Prior art S/I tubing is currently made from PVC and is very thick walled to prevent the tube from kinking or collapsing under vacuum. With the process of the invention, the following benefits can be achieved—the tubing would be kink resistant yet have thin walls and therefore be lightweight, cost would be comparable to PVC without the environmental concern, thus, it would reduce the overall amount of plastic used. Currently, S/I tubes have 1 to 2 lbs of PVC tubing in them. The S/I tubing of the invention would reduce the overall weight of plastic to approximately $\frac{1}{10}$ of a pound and would be easier for the surgeon to use. In addition, the wire in the irrigation tube could be electrically heated to allow the fluid to be at or near body temperature when introduced to the patient.

Insufflation tubing: This tubing is used to deliver carbon dioxide gas for laparoscopic surgery and has some of the same problems as S/I tubing. Lighter weight and less plastic wasteful tubing could be made, and the heating element in the wall would be of benefit to the patient by allowing body temperature gas to be introduced instead of colder gas.

Vacuum tube: The process of the invention would be beneficial to any situation, either medical or non-medical, where the need exists for a vacuum tube to be thin walled and preferably kink resistant. This process could also be used to produce thin walled pressure tubes.

Split sheath introducers: The process of the invention can be modified to make a split sheath introducer. The wire extrusion can be wound on a special mandrel to make a semicircular tube on each side of the mandrel and then fusing or bonding the split sheath together.

Tracheostomy tubes: Thin walled kink-free tracheostomy tubes would benefit from the process of the invention. The balloon-filled lumen could be easily fused or bonded together along with the breathing tube. The same advantages would apply to crycothyrodectomy tubes used in emergency situations.

Intubation tubes: The intubation tubes have very thin walls and are very kink resistant which would help enormously with these devices especially in pediatrics or cases where the trachea has become constricted. The flexibility would make them ideal for nasal tubes as well.

G-tubes/J-tubes: Gastronomy and jujenostomy tubes are used for enteral feeding and would likewise benefit from reduced diameters, enhanced column strength for insertion, and kink resistance for safety.

ERCP catheters: Extracoporeal retrograde cholangeopancreatography catheters are very long catheters typically used to treat gallstones in the cystic duct. These would benefit from the increased column strength and reduced wall thickness as well as high kink resistance.

Endoscope shafts: Flexible and steerable endoscopes require shafts that can give good protection to the internal components as well as provide regions of variable flexibility and good column stiffness throughout. The shafts must also accommodate multiple lumens.

Drainage tubes: Drainage and suction tubes would also benefit from thin walls, lightweight and kink resistance.

Guide catheters: Guide catheters commonly used in cardiology to gain access to the coronary arteries are carefully designed to meet various design criteria such as shape, stiffness, steerability, torque strength and kink resistance. They have to be smooth and non-thrombogenic. The bonding and fusing process of the invention can serve as a good basis of construction for these devices. Torque strength or torqability can be improved in devices of the invention by putting relatively stiff elements along the length of the shaft or by altering the plastic used to extrude over the wire.

Hydrocephalic shunts. A common problem with these shunts, which are used to drain excess hydrocephalic fluid from the ventricles of the brain, is that they can kink and prevent adequate drainage. This in turn can require a revision to be performed or merely patient discomfort and possibly increase the chances of an infection. By producing portions of them with the process of the invention, it is possible to create very crush as well as kink resistant shunts.

Guidewires: Guidewires are used in a number of applications including urology and radiology. They are commonly constructed with close wound stainless steel springs and then coated with Teflon or a plastic for lubricity. They are typically 2 to 6 feet long and are around 1 mm in diameter or less. These structures can be fabricated with the process of the invention.

Angioplasty and dilation balloons: The catheters that these balloons are placed on require the ability to transmit as much as 15 atmospheres or more over a 3-foot or longer length. Here again the advantages of reinforced thin walls with excellent column strength would be very helpful.

Vascular grafts: A variety of graft designs are commonly used and these include designs for aortic grafts, dialysis grafts, bypass grafts, arterial grafts for various locations in the peripheral vasculature. All of these will benefit from kink resistance and crush resistance as well as excellent flexibility. Various coatings and surface modifications can be applied.

Cholangiography catheters: Catheters used to deliver contrast media to the cystic duct are difficult to use as the conflicting requirements of kink resistance and thin walls make necessary a compromise. This is not the case with the tubing of the invention where the wall can be kept very thin and kink resistant.

Vascular embolectomy/thrombectomy catheters: These small diameter catheters have balloons on them for removing clots and in the case of thrombectomy they have a spring body which would make the process of the invention a natural for them. As for the embolectomy catheters, they may benefit from the educed profile, increased inflation lumen and guidewire lumens.

Central venous catheters: These catheters are placed near the clavicle and access the superior vena cava through one of the subclavian or innominate veins. They are used for emergency treatment in the case of kidney failure among other uses. These catheters are frequently constructed with two and three lumens and require the ability to extract and return blood quickly. They would benefit from the processes of the invention in that the walls can be made thinner for increased flow or reduced profile or both. They would be almost kink proof and they would have tremendous column strength which would aid in insertion. The processes of the invention would not interfere with any of the commonly used coatings and they may show up better on ultrasound.

The foregoing disclosure and description of the invention are illustrative and explanatory thereof, and various changes in the size, shape and materials, as well as in the details of the illustrated construction, may be made without departing from the spirit and scope of the invention. For these reasons, the above description should not be construed as limiting the invention, but should be interpreted as merely exemplary of preferred embodiments.

We claim:

1. A method of manufacturing a kink-resistant tube, comprising the steps of winding a wire having a coating around a mandrel while simultaneously heating the coated wire, to thereby melt the coating around the wound wire to form a tube; and adjusting speed of the winding and temperatures of heating of the coated wire based on material and diameter of the coated wire and diameter of the mandrel.

2. The method of claim 1, wherein the wire comprises a metal.

3. The method of claim 1, wherein the coating comprises a thermoplastic.

4. The method of claim 1, wherein the coated wire is heated with at least one hot air gun.

5. The method of claim 1, further comprising the step of providing a means for smoothing the melted coating along the surface of the tube.

6. The method of claim 5, wherein the means for smoothing the melting coating comprises a roller.

7. The method of claim 6, wherein the roller is heated.

8. The method of claim 6, further comprising a means for controlling the tension of the roller against the tube.

9. The method of claim 8, wherein the means for controlling the tension of the roller against the tube comprises a tension spring.

10. The method of claim 5, wherein the means for smoothing the melting coating comprises a die.

11. The method of claim 1, wherein the mandrel has a circular cross-section.

12. The method of claim 1, wherein at least a portion of the mandrel has a noncircular cross-section.

13. The method of claim 1, wherein the mandrel has a variable diameter along the length of the mandrel.

14. The method of claim 1, wherein the coated wire is wound around the mandrel with a variable pitch to produce a tube with variable flexibility.

15. The method of claim 1, wherein the wire comprises a nonmetal.

16. The method of claim 1, wherein the wire comprises a braided material.

17. The method of claim 1, wherein two or more coated wires are wound around the mandrel.

18. The method of claim 1, further comprising the step of providing a means for imparting a textured surface to the tube.

19. The method of claim 18, wherein the means for imparting a textured surface to the tube is a textured roller applied against the surface of the tube.

20. A method of manufacturing a kink-resistant tube, comprising the steps of:
    placing a mandrel between two spindles of a winding machine;
    winding a co-extruded wire comprising a core coated in a thermoplastic polymer around the mandrel about three to four times;
    attaching the end of the co-extruded wire to the spindle;
    starting the winding machine and winding the co-extruded wire over the mandrel while simultaneously applying heat from at least one hot air gun to melt the thermoplastic polymer as it is wound around the mandrel, with a heated roller trailing and positioned near the hot air gun to smooth the surface of the melted thermoplastic polymer, to thereby form a tube;
    adjusting speed of the winding machine and temperatures of the hot air and heated roller based on material and diameter of the co-extruded wire and diameter of the mandrel;
    when the winding is complete, cutting the co-extruded wire close to the mandrel and removing the mandrel with the tube from the winding machine; and
    removing the tube from the mandrel.

21. The method of claim 20, wherein the co-extruded wire core comprises a metal.

22. The method of claim 20, wherein the mandrel having a constant cross sectional geometric shape along its length and a carrying diameter.

* * * * *